US009458067B2

(12) United States Patent
Becker et al.

(10) Patent No.: US 9,458,067 B2
(45) Date of Patent: *Oct. 4, 2016

(54) PROCESS FOR PRODUCING CYCLOHEXYLBENZENE

(71) Applicant: ExxonMobil Chemical Patents Inc., Baytown, TX (US)

(72) Inventors: Christopher L. Becker, Manhattan, KS (US); Hari Nair, Houston, TX (US); James R. Lattner, LaPorte, TX (US); Keith H. Kuechler, Friendswood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 198 days.

This patent is subject to a terminal disclaimer.

(21) Appl. No.: 14/373,690

(22) PCT Filed: Jan. 28, 2013

(86) PCT No.: PCT/US2013/023437
§ 371 (c)(1),
(2) Date: Jul. 22, 2014

(87) PCT Pub. No.: WO2013/119407
PCT Pub. Date: Aug. 15, 2013

(65) Prior Publication Data
US 2015/0011812 A1    Jan. 8, 2015

Related U.S. Application Data

(60) Provisional application No. 61/596,442, filed on Feb. 8, 2012.

(51) Int. Cl.
*C07C 2/74* (2006.01)
*C07C 5/367* (2006.01)
(Continued)

(52) U.S. Cl.
CPC ............... *C07C 2/74* (2013.01); *C07C 5/367* (2013.01); *C07C 37/08* (2013.01); *C07C 45/53* (2013.01);

(Continued)

(58) Field of Classification Search
None
See application file for complete search history.

(56) References Cited

U.S. PATENT DOCUMENTS 3,412,165 A    11/1968    Slaugh et al.
3,536,771 A    10/1970    De Graff
(Continued)

FOREIGN PATENT DOCUMENTS

EP    0 293 032    11/1988
EP    0 338 734    10/1989
(Continued)

OTHER PUBLICATIONS

Borodina et al., "Hydroalkylation of Benzene and Ethylbenzene Over Metal Containing Zeolite Catalysts", Microporous and Mesoporous Materials, 2007, vol. 105, pp. 181-188.
(Continued)

*Primary Examiner* — In Suk Bullock
*Assistant Examiner* — Philip Louie
(74) *Attorney, Agent, or Firm* — Stephen A. Baehl (57) ABSTRACT

In a process for producing cyclohexylbenzene, hydrogen and benzene are introduced to a first hydroalkylation reaction zone which contains a hydroalkylation catalyst and which is operated under at least partly liquid phase conditions sufficient to effect hydroalkylation of benzene to produce a mixed liquid/vapor phase effluent comprising cyclohexylbenzene and unreacted benzene, wherein at least a portion of the unreacted benzene is in the vapor phase. At least a portion of the effluent is cooled to condense a liquid phase stream containing at least some of the cyclohexylbenzene in the effluent portion and leave a residual stream containing at least some of the unreacted benzene and cyclohexylbenzene. At least a portion of the liquid stream is recycled to the first hydroalkylation reaction zone or to contact the mixed phase effluent exiting the first hydroalkylation reaction zone. Other methods of cooling the reaction effluent are disclosed.

10 Claims, 4 Drawing Sheets

(51) Int. Cl.
*C07C 37/08* (2006.01)
*C07C 45/53* (2006.01)
*C07C 407/00* (2006.01)

(52) U.S. Cl.
CPC ......... *C07C 407/00* (2013.01); *C07C 2101/14* (2013.01); *C07C 2529/08* (2013.01); *C07C 2529/18* (2013.01); *C07C 2529/70* (2013.01); *Y02P 20/582* (2015.11)

(56) References Cited

U.S. PATENT DOCUMENTS

| | | | |
|---|---|---|---|
| 3,760,018 | A | 9/1973 | Suggitt et al. |
| 3,784,617 | A | 1/1974 | Suggitt et al. |
| 3,784,618 | A | 1/1974 | Suggitt et al. |
| 3,839,477 | A | 10/1974 | Suggitt et al. |
| 3,864,421 | A | 2/1975 | Suggitt |
| 3,957,687 | A | 5/1976 | Arkell et al. |
| 3,962,362 | A | 6/1976 | Suggitt |
| 4,021,490 | A | 5/1977 | Hudson |
| 4,094,918 | A | 6/1978 | Murtha et al. |
| 4,122,125 | A | 10/1978 | Murtha et al. |
| 4,152,362 | A | 5/1979 | Murtha |
| 4,177,165 | A | 12/1979 | Murtha et al. |
| 4,206,082 | A | 6/1980 | Murtha et al. |
| 4,219,689 | A | 8/1980 | Murtha |
| 4,268,699 | A | 5/1981 | Murtha et al. |
| 4,329,531 | A | 5/1982 | Murtha et al. |
| 4,439,409 | A | 3/1984 | Puppe et al. |
| 4,447,554 | A | 5/1984 | Murtha et al. |
| 4,826,667 | A | 5/1989 | Zones et al. |
| 4,954,325 | A | 9/1990 | Rubin et al. |
| 5,236,575 | A | 8/1993 | Bennett et al. |
| 5,250,277 | A | 10/1993 | Kresge et al. |
| 5,334,795 | A | 8/1994 | Chu et al. |
| 5,362,697 | A | 11/1994 | Fung et al. |
| 5,557,024 | A | 9/1996 | Cheng et al. |
| 6,037,513 | A | 3/2000 | Chang et al. |
| 6,077,498 | A | 6/2000 | Diaz Cabañas et al. |
| 6,489,529 | B1 | 12/2002 | Cheng et al. |
| 6,506,953 | B1 | 1/2003 | Cheng et al. |
| 6,720,462 | B2 | 4/2004 | Duda et al. |
| 6,730,625 | B1 | 5/2004 | Chang et al. |
| 6,756,030 | B1 | 6/2004 | Rohde et al. |
| 6,936,744 | B1 | 8/2005 | Cheng et al. |
| 8,084,648 | B2 | 12/2011 | Buchanan et al. |
| 2004/0092757 | A1 | 5/2004 | Oguchi et al. |
| 2005/0158238 | A1 | 7/2005 | Tatsumi et al. |
| 2008/0027256 | A1 | 1/2008 | Roth et al. |
| 2008/0027259 | A1 | 1/2008 | Roth et al. |
| 2008/0045768 | A1 | 2/2008 | Roth et al. |
| 2010/0317895 | A1 | 12/2010 | Buchanan et al. |
| 2011/0037022 | A1 | 2/2011 | Dakka et al. |

FOREIGN PATENT DOCUMENTS

| | | |
|---|---|---|
| WO | WO 95/31421 | 11/1995 |
| WO | WO 97/17290 | 5/1997 |
| WO | WO 01/53236 | 7/2001 |
| WO | WO 01/74767 | 10/2001 |
| WO | WO 2005/118476 | 12/2005 |
| WO | 2009/025939 | 2/2009 |
| WO | WO 2009/038900 | 3/2009 |
| WO | 2009/102517 | 8/2009 |
| WO | WO 2013/058882 | 4/2013 |

OTHER PUBLICATIONS

Fan et al., "Synthesis and Catalytic Properties of a New Titanosilicate Molecular Sieve with the Structure Analogous to MWW-type Lamellar Precursor", Journal of Catalyst, 2006, vol. 243, pp. 183-191.

Kim et al., "Structural Evolution of B-MCM-36 and B-ITQ-2 from B-MCM-22", Bull. Korean Chem. Society, 2006, vol. 27, No. 10, pp. 1693-1696.

Lawton et al., "Zeolite MCM-49: A Three-Dimensional MCM-22 Analogue Synthesized by in Situ Crystallization", Journal of Physical Chemistry, 1996, vol. 100, pp. 3788-3798.

Maheshwari et al., "Layer Structure Preservation During Swelling, Pillaring, and Exfoliation of a Zeolite Precursor", Journal of American Chemical Society, 2008, vol. 130, pp. 1507-1516.

Ruan et al., "Structure Elucidation of the Highly Active Titanosilicate Catalyst Ti-YNU-1", Angew. Chem. Int. Ed. 2005, vol. 44, pp. 6719-6723.

Slaugh et al., "Hydrodimerization of Benzene to Phenylcyclohexane over Supported Transition Metal Catalysts", Journal of Catalysis, 1969, vol. 13, pp. 385-396.

Wu et al., "Methodology for Synthesizing Crystalline Metallosilicates with Expanded Pore Windows Through Molecular Alkoxysilylation of Zeolitic Lamellar Precursors", Journal of American Chemical Society, 2008, vol. 130, pp. 8178-8187.

Zhicheng et al., "Static Synthesis of High-Quality MCM-22 Zeolite with High $SiO_2/Al_2O_3$ Ratio", Chinese Science Bull, 2004, vol. 49, No. 6, pp. 556-561.

PROCESS FOR PRODUCING CYCLOHEXYLBENZENE

PRIORITY CLAIM

This application is a National Stage Application of International Application No. PCT/US2013/023437 filed Jan. 28, 2013, which claims the benefit of Provisional Application No. 61/596,442, filed Feb. 8, 2012, the disclosures of which are incorporated by their reference in its entirety.

FIELD

The present invention relates to a process for producing cyclohexylbenzene and for converting the resultant cyclohexylbenzene into phenol and cyclohexanone.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide, and then cleavage of the hydroperoxide to produce equimolar amounts of phenol and acetone. However, the world demand for phenol is growing more rapidly than that for acetone. In addition, due to a developing shortage, the cost of propylene is likely to increase.

Thus, a process that uses higher alkenes instead of propylene as feed and coproduces higher ketones, such as cyclohexanone, rather than acetone may be an attractive alternative route to the production of phenols. For example, there is a growing market for cyclohexanone, which is used as an industrial solvent, as an activator in oxidation reactions and in the production of adipic acid, cyclohexanone resins, cyclohexanone oxime, caprolactam, and nylon 6.

It is known from, for example, U.S. Pat. No. 6,037,513 that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt, and mixtures thereof. The contacting is conducted at a temperature of about 50° C. to 350° C., a pressure of about 100 kPa to 7000 kPa, a benzene to hydrogen molar ratio of about 0.01 to 100 and a WHSV of about 0.01 to 100. The '513 patent also discloses that the resultant cyclohexylbenzene can be oxidized to the corresponding hydroperoxide which is then decomposed to the desired phenol and cyclohexanone co-product.

However, although benzene hydroalkylation is an attractive route for the production of cyclohexylbenzene, with current processes the selectivity to the desired cyclohexylbenzene product becomes undesirably low at conversions much above 30%. In addition, the hydroalkylation of benzene over an acid catalyst, such as MCM-22, is highly exothermic and high temperatures are an important factor leading to reduced cyclohexylbenzene selectivity. The major impurities in the product are cyclohexane and dicyclohexylbenzene. Cyclohexane builds up in the $C_6$ recycle streams and must be removed by treatment or purging, whereas the dicyclohexylbenzene by-product requires transalkylation. Although transalkylation of dicyclohexylbenzene with benzene produces additional cyclohexylbenzene product, the cost of transalkylation is not insignificant. There is therefore a need to provide a benzene hydroalkylation process which provides improved selectivity to monocyclohexylbenzene at acceptable benzene conversion rates.

U.S. Pat. No. 3,784,617 discloses a process for the hydroalkylation of mononuclear aromatic compounds, in which an aromatic charge, such as benzene, and a first portion of hydrogen are reacted in a first stage to produce a partially hydroalkylated stream and, after cooling, the partially hydroalkylated stream and a second portion of hydrogen are reacted in a second stage to produce a hydroalkylate product. Introducing the hydrogen in multiple stages reduces the degree of benzene conversion, and hence the temperature rise, in each stage. By avoiding excessive temperature increases, more favorable product selectivities are said to be obtained.

U.S. Patent Publication No. 2010/0317895 discloses a process for producing cyclohexylbenzene, the process comprising: (a) introducing hydrogen and a liquid feed comprising benzene into a reaction zone; (b) contacting the benzene with the hydrogen in the reaction zone under hydroalkylation conditions to produce cyclohexylbenzene; (c) removing an effluent stream comprising cyclohexylbenzene and unreacted benzene from said reaction zone; (d) dividing the effluent stream into at least first and second portions; (e) cooling the effluent stream first portion; and (f) recycling the cooled effluent stream first portion to the reaction zone, wherein the ratio of the mass of the effluent stream first portion to the mass of effluent stream second portion is at least 2:1. At least part of the effluent stream second portion may be cooled and fed to at least one further reaction zone where the unreacted benzene in the effluent stream second portion is contacted with further hydrogen under hydroalkylation conditions to produce further cyclohexylbenzene.

The present invention seeks to provide improved designs for providing temperature control of the reagents in benzene hydroalkylation processes and particularly those employing staged addition of the hydrogen.

SUMMARY

In one aspect, the invention resides in a process for producing cyclohexylbenzene comprising:

A process for producing cyclohexylbenzene comprising:

(a) introducing hydrogen and benzene to a first hydroalkylation reaction zone containing a hydroalkylation catalyst;

(b) operating said first hydroalkylation reaction zone under at least partly liquid phase conditions sufficient to effect hydroalkylation of at least a portion of the benzene in the presence of said hydroalkylation catalyst to produce a first mixture exiting the first reaction zone comprising a liquid phase and a vapor phase;

(c) separating the first mixture into a first liquid effluent comprising cyclohexylbenzene and a portion of unreacted benzene and a first vapor effluent comprising a portion of the unreacted benzene;

(d) cooling at least a portion of the first vapor effluent to obtain a second liquid effluent containing at least a portion of the unreacted benzene; and (e) recycling at least a portion of the second liquid phase stream to the first hydroalkylation reaction zone or to contact the first mixture or to mix with the first liquid effluent.

In one embodiment, the process further comprises:

(f) introducing at least a portion of the first liquid effluent and additional hydrogen to a second hydroalkylation reaction zone containing a hydroalkylation catalyst and connected in series with the first hydroalkylation reaction zone; and (g) operating said second hydroalkylation reaction zone under at least partly liquid phase conditions sufficient to effect hydroalkylation of at least a portion of the unreacted benzene in the first liquid effluent in the presence of said hydroalkylation catalyst to produce a third liquid effluent comprising cyclohexylbenzene.

Conveniently, the cooling (c) is effected by passing the effluent portion through a heat exchanger to supply heat to a feed to another portion of the process. In one embodiment, the heat exchanger supplies heat to a reboiler for a benzene distillation column. In another embodiment, heat exchanger supplies heat to the feed to a dehydrogenation reactor for converting cyclohexane produced as a by-product of said operating steps (b) and (f) to benzene.

In another aspect, the invention resides in a process for producing cyclohexylbenzene comprising:

(a) introducing hydrogen and benzene to a first hydroalkylation reaction zone;

(b) operating said first hydroalkylation reaction zone under at least partly liquid phase conditions sufficient to effect hydroalkylation of benzene in the presence of said hydroalkylation catalyst to produce an effluent comprising cyclohexylbenzene and unreacted benzene; and (c) cooling at least a portion of the effluent by contacting said effluent portion with a coolant to produce a cooled combined stream.

In one embodiment, the process further comprises:

(d) introducing said cooled combined stream to a second hydroalkylation reaction zone; and (e) operating said second hydroalkylation reaction zone under at least partly liquid phase conditions sufficient to cause hydroalkylation of unreacted benzene in said combined stream in the presence of said hydroalkylation catalyst to produce a second effluent comprising cyclohexylbenzene.

Conveniently, the cooling (c) reduces the temperature of said combined stream by at least 10° C., such as at least 20° C., as compared with the temperature of the effluent exiting said first hydroalkylation reaction zone.

In a further aspect, the invention resides in a process for producing cyclohexylbenzene comprising:

(a) introducing hydrogen and benzene to a first hydroalkylation reaction zone containing a hydroalkylation catalyst;

(b) operating said first hydroalkylation reaction zone under at least partly liquid phase conditions sufficient to effect hydroalkylation of benzene in the presence of said hydroalkylation catalyst to produce a mixed liquid/vapor phase effluent comprising cyclohexylbenzene and unreacted hydrogen and benzene, wherein at least a portion of the unreacted benzene is in the vapor phase;

(c) removing said mixed phase first effluent from said first hydroalkylation reaction zone;

(d) cooling at least a portion of the mixed phase first effluent removed from said first hydroalkylation reaction zone by heat exchange with a feed to another portion of the process;

(e) introducing at least a portion of the cooled mixed phase first effluent to a second hydroalkylation reaction zone containing a hydroalkylation catalyst and connected in series with the first hydroalkylation reaction zone; and (f) operating said second hydroalkylation reaction zone under at least partly liquid phase conditions sufficient to effect hydroalkylation of unreacted benzene in mixed phase first effluent in the presence of said hydroalkylation catalyst to produce a second effluent comprising cyclohexylbenzene.

In a further aspect, the invention resides in a process for coproducing phenol and cyclohexanone, the process comprising producing cyclohexylbenzene by the process described herein, oxidizing the cyclohexylbenzene to produce cyclohexylbenzene hydroperoxide, and cleaving the cyclohexylbenzene hydroperoxide to produce phenol and cyclohexanone.

DETAILED DESCRIPTION OF THE EMBODIMENTS

Described herein is a process for producing cyclohexylbenzene by the hydroalkylation of benzene, particularly by a multi-stage process with or without staged addition of hydrogen, in which various cooling schemes are provided to improve product selectivity.

In one preferred embodiment, the present process forms part of an integrated process for producing phenol from benzene in which the cyclohexylbenzene produced in the benzene hydroalkylation reaction is oxidized to produce cyclohexylbenzene hydroperoxide and the hydroperoxide is cleaved to produce phenol and cyclohexanone. The ensuing description will therefore focus on this integrated process.

Production of the Cyclohexylbenzene

The initial step of the integrated process for producing phenol is the selective hydroalkylation of benzene in the presence of a bifunctional hydroalkylation catalyst. The hydroalkylation reaction produces cyclohexylbenzene (CHB) according to the following reaction:

Any commercially available benzene feed can be used in the hydroalkylation reaction, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically, the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica, and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia, and Florida clays or others in which the main mineral constituent is halloysite, kaolinite, dickite, nacrite, or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as, ternary compositions such as silica-alumina-thoria, silica-alumina-zirconia, silica-alumina-magnesia, and silica-magnesia-zirconia.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. In this respect, the term "reaction zone" is used herein to define the portion of a reactor containing the hydroalkylation catalyst so that, in the case of a multi-zone process, the different reaction zones can be located in a single reactor or in multiple reactors. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The product of the hydroalkylation reaction is a mixed liquid/vapor phase effluent comprising cyclohexylbenzene and unreacted benzene, at least a portion of which is in the vapor phase, possibly with some unreacted hydrogen. As used herein, "unreacted benzene" and "unreacted hydrogen" mean benzene and hydrogen, respectively, that is not consumed in the hydroalkylation reaction. The hydroalkylation reaction is highly exothermic and hence to avoid excessive temperature rises during the reaction, together with the attendant loss in product selectivity, the present process includes provision for reducing the temperature of the reagents and/or products of the hydroalkylation reaction, or, in the case of a multi-stage reaction, the inter-stage reaction effluent.

In a first embodiment, the temperature reduction is achieved by separating the first mixture exiting the first reaction zone comprising a liquid phase and a vapor phase into a first liquid effluent and a first vapor effluent, cooling at least a portion of the first vapor effluent to obtain a second liquid effluent comprising at least a portion of the unreacted benzene, followed by recycling at least a portion of the second liquid effluent to the first reaction zone, or to contact the first mixture, or to mix with the first liquid effluent. Due to the boiling point differential, the first liquid effluent comprises cyclohexylbenzene and a portion of the unreacted benzene, and the first vapor phase comprises a portion of the unreacted benzene and optionally a small amount of cyclohexylbenzene, if any at all. Accordingly, the second liquid effluent may comprise at least 90 wt %, such as at least 93 wt %, or at least 95 wt %, or at least 98 wt %, or at least 99 wt %, of benzene. In exemplary embodiments, the benzene contained in the second liquid effluent constitutes at least 1 wt % of the total weight of the first mixture exiting the first reaction zone. In other embodiments, the benzene contained in the first liquid effluent constitutes at least 3 wt % of the total weight of the first mixture existing the first reaction zone, or at least 5 wt %, or at least 8 wt %, or at least 10 wt %, thereof. The first liquid effluent may comprise from 3 wt % to 20 wt %, such as from 5 wt % to 15 wt %, such as from 8 wt % to 12%, such as from 10 wt % to 12 wt %, of cyclohexylbenzene, based on the total weight of the first liquid effluent.

At least a portion of the liquid stream is then recycled either to contact the reagents in the reaction zone or to contact the mixed phase effluent exiting the reaction zone. Typically, the cooling is effected by passing the effluent portion through a heat exchanger. The heat exchanger may be used to supply heat to another portion of the process. For example, the heat exchanger can be used to supply heat to a reboiler for a benzene distillation column or to supply heat to the feed to a dehydrogenation reactor for producing benzene from cyclohexane produced as a by-product of the hydroalkylation reaction.

Where the hydroalkylation reaction is performed in a plurality of reaction zones, at least a portion of the residual stream and additional hydrogen may then be supplied to a downstream reaction zone containing a hydroalkylation catalyst and connected in series with the first-mentioned reaction zone.

The second hydroalkylation reaction zone may be operated under at least partly liquid phase conditions sufficient to effect hydroalkylation of unreacted benzene in residual stream portion in the presence of said hydroalkylation catalyst to produce a second effluent comprising cyclohexylbenenze. At least a portion of the second effluent may be cooled to condense a second liquid phase stream containing at least some of the cyclohexylbenzene and leave a second residual stream containing at least some of the unreacted benzene and cyclohexylbenzene. At least a portion of the second liquid stream may be recycled to the second hydroalkylation reaction zone or to contact the second mixed liquid/vapor phase effluent exiting the second hydroalkylation reaction zone.

In a second embodiment, the temperature reduction is achieved by combining least a portion of the reaction effluent exiting a given reaction zone with a coolant, such as additional hydrogen and/or an inert gas, to produce a cooled combined stream. Where the hydroalkylation reaction is performed in a plurality of reaction zones, at least a portion of combined stream containing the additional hydrogen may then be supplied to a downstream reaction zone containing a hydroalkylation catalyst and connected in series with the first-mentioned reaction zone.

In a third embodiment, the hydroalkylation reaction is performed in a plurality of reaction zones, at least a portion of the mixed phase first effluent removed from a first hydroalkylation reaction zone is cooled by heat exchange with a feed to another portion of the process and the cooled mixed phase first effluent portion is then supplied, normally with additional hydrogen, to a second hydroalkylation reaction zone containing a hydroalkylation catalyst and connected in series with the first hydroalkylation reaction zone. As in the first embodiment, the heat exchange can be used to supply heat to a reboiler for a benzene distillation column or to supply heat to the feed to a dehydrogenation reactor for producing benzene from cyclohexane produced as a by-product of the hydroalkylation reaction.

Treatment of the Cyclohexylbenzene Product

Although the hydroalkylation reaction using an MCM-22 family zeolite catalyst is highly selective towards cyclohexylbenzene, the hydroalkylation reaction will inevitably produce certain by-products. As stated previously, a prevalent by-product is normally cyclohexane, but generally the reaction effluent will also contain dicyclohexylbenzene, tricyclobenzene and even heavier alkylates, and methylcyclopentane. Methylcyclopentane is also generated in the transalkylation reaction described in more detail below.

To recover the various components, the hydroalkylation reaction effluent is normally fractionated to separate the effluent into one or more $C_6$ fractions containing most of the unreacted benzene and most of the cyclohexane and methylcyclopentane by-products, a $C_{12}$ fraction containing most of the cyclohexylbenzene product, and a $C_{18}$ fraction containing most of the dicyclohexylbenzene by-product, and possibly a $C_{24}$ or higher product heavy alkylate by-product.

In one embodiment, the fractionation of the hydroalkylation reaction effluent produces a single $C_6$ fraction and this $C_6$ fraction is then contacted with a dehydrogenation catalyst under dehydrogenation conditions sufficient to convert at least part of the cyclohexane in the $C_6$ fraction to benzene, but to change amount of methylcyclopentane by no more than 10% of the total amount of the $C_6$ fraction contacted with the dehydrogenation catalyst, said amounts on a weight basis. Generally, the dehydrogenation is arranged to convert at least 25 wt %, such at least 50 wt %, for example at least 90 wt % of the cyclohexane in the $C_6$ fraction to benzene but to change the amount of methylcyclopentane by no more 5 wt %, such as no more than 2 wt %, or no more than 1 wt %, or no more than 0.5 wt %, or no more than 0.1 wt % of the total amount of the $C_6$ fraction contacted with the dehydrogenation catalyst. A suitable catalyst to effect the desired dehydrogenation comprises an inorganic support comprising 0.05 wt % to 0.5 wt % of a metal selected from Group 14 of the Periodic Table of Elements; such as tin, and 0.1 wt % to 2 wt % of a metal selected from Groups 6 to 10 of the Periodic Table of Elements, such as platinum and/or palladium, the wt %s being based upon total weight of the first catalyst.

Conveniently, the support is selected from the group consisting of silica, a silicate, an aluminosilicate, zirconia, and carbon nanotubes, and preferably comprises silica. Suitable dehydrogenation conditions include a temperature of about 250° C. to about 500° C., a pressure of about 100 kPa to 7000 kPa, a weight hourly space velocity of about 0.2 $hr^{-1}$ to 50 $hr^{-1}$, and a hydrogen to hydrocarbon feed molar ratio of about 0 to about 20.

After removal of the hydrogen, the dehydrogenation effluent typically contains at least 25 wt %, such at least 50 wt %, for example at least 90 wt % benzene, from about 0.1 wt % to about 10 wt %, such as from about 1 wt % to about 5 wt %, cyclohexane and from about 0.1 wt % to about 5 wt %, such as from about 0.5 wt % to about 1 wt %, methylcyclopentane. The dehydrogenation effluent is then fractionated to produce a major fraction rich in benzene and a minor fraction rich in methylcyclopentane. The benzene-rich fraction typically comprises from about 90 wt % to about 99 wt % of the liquid dehydrogenation effluent and contains no more than 5 wt %, normally at least 0.01 wt %, such as about 0.1 wt % to about 1 wt %, methylcyclopentane, possibly no detectable methylcyclopentane, and from about 0.1 wt % to about 10 wt % cyclohexane, such as from about 0.5 wt % to about 5 wt % cyclohexane. The methylcyclopentane-rich fraction typically comprises from about 1 wt % to about 10 wt % of the liquid dehydrogenation effluent and contains from about 5 wt % to about 50 wt % methylcyclopentane, from about 5 wt % to about 50 wt % cyclohexane and from about 10 wt % to about 80 wt % benzene. The benzene fraction is recycled to the hydroalkylation reaction, whereas the methylcyclopentane-rich fraction is normally recovered for use as a motor gasoline blendstock.

In another embodiment, the fractionation of the hydroalkylation reaction effluent produces at least two $C_6$ fractions, namely a first, methylcyclopentane containing fraction and a second, benzene-containing fraction. The first fraction typically comprises from about 1 wt % to about 10 wt % of the liquid hydroalkylation reaction effluent and contains from about 1 to about 99 wt %, such as from about 2 wt % to about 80 wt %, of the methylcyclopentane contained in hydroalkylation reaction effluent. Thus the first fraction generally contains from about 5 to about 50 wt % methylcyclopentane, together with about 5 wt % to about 50 wt % cyclohexane and about 10 wt % to about 80 wt % benzene. The second fraction typically comprises from about 90 wt % to about 99 wt % of the liquid hydroalkylation effluent and contains up to 5 wt %, such as from about 0.01 wt % to about 1 wt %, methylcyclopentane, possibly no detectable methylcyclopentane, the reminder being composed mainly of benzene and cyclohexane. The second fraction is therefore subjected to the dehydrogenation reaction discussed above, while the first fraction is normally recovered for use as a motor gasoline blendstock.

As discussed above, fractionation of the hydroalkylation reaction effluent also produces a $C_{12}$ fraction containing most of the cyclohexylbenzene and a $C_{18}$ fraction containing most of the dicyclohexylbenzene. The cyclohexylbenzene is fed to the oxidation step discussed below whereas, depending on the amount of the dicyclohexylbenzene produced, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 $hr^{-1}$ to about 10 $hr^{-1}$ on total feed, and a benzene/dicyclohexylbenzene weight ratio about of 1:1 to about 5:1. The transalkylation reaction can, and typically will, generate additional methylcyclopentane.

Dealkylation or cracking is also typically effected in a reactor separate from the hydroalkylation reactor, such as a reactive distillation unit, at a temperature of about 150° C. to about 500° C. and a pressure of 200 kPa to 3550 kPa over an acid catalyst such as an aluminosilicate, an aluminophosphate, a silicoaluminophosphate, amorphous silica-alumina, an acidic clay, a mixed metal oxide, such as $WO_x/ZrO_2$, phosphoric acid, sulfated zirconia, and mixtures thereof. Generally, the acid catalyst includes at least one aluminosilicate, aluminophosphate or silicoaluminophosphate of the FAU, AEL, AFI, and MWW family. Unlike transalkylation, Dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

It is to be appreciated that the transalkylation and dealkylation reactions can, and typically will generate, additional methylcyclopentane and hence the products of these reactions can be subjected to the separation steps described above to generate the $C_6$ fraction(s), which may subsequently be subjected to dehydrogenation.

Cyclohexylbenzene Oxidation

In order to convert the cyclohexylbenzene into phenol and cyclohexanone, the cyclohexylbenzene may be oxidized to the corresponding hydroperoxide. This is accomplished by contacting the cyclohexylbenzene with oxygen (e.g., an oxygen-containing gas, such as air and various derivatives of air). For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N', N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl- 1-phenyl-1-hydroperoxide, based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent may be subjected to a cleavage reaction, with or without undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary, nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Publication No. WO 2009/025939.

Hydroperoxide Cleavage

Another reactive step in the conversion of the cyclohexylbenzene into phenol and cyclohexanone involves the acid-catalyzed cleavage of the cyclohexyl-1-phenyl-1-hydroperoxide produced in the oxidation step.

Generally, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to no greater than 3000 wppm, or at least 150 wppm to and no greater than 2000 wppm of the acid catalyst, or at least 300 wppm and no greater than 1500 wppm of the acid catalyst, based upon total weight of the cleavage reaction mixture.

In other embodiments, a heterogeneous acid catalyst is employed for the cleavage reaction, such as molecular sieve, and in particular a molecular sieve having a pore size in excess of 7 Å. Examples of suitable molecular sieves include zeolite beta, zeolite Y, zeolite X, ZSM-12, and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction, but also to increase the selectivity of the conversion to phenol and cyclohexanone.

Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Generally, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon 6, and nylon 6,6.

The phenol produced through the processes disclosed herein may be used, for example, to produce phenolic resins, bisphenol A, ε-caprolactam, adipic acid, and/or plasticizers.

The invention will now be more particularly described with reference to the accompanying drawings and the following non-limiting examples.

Figure 1:
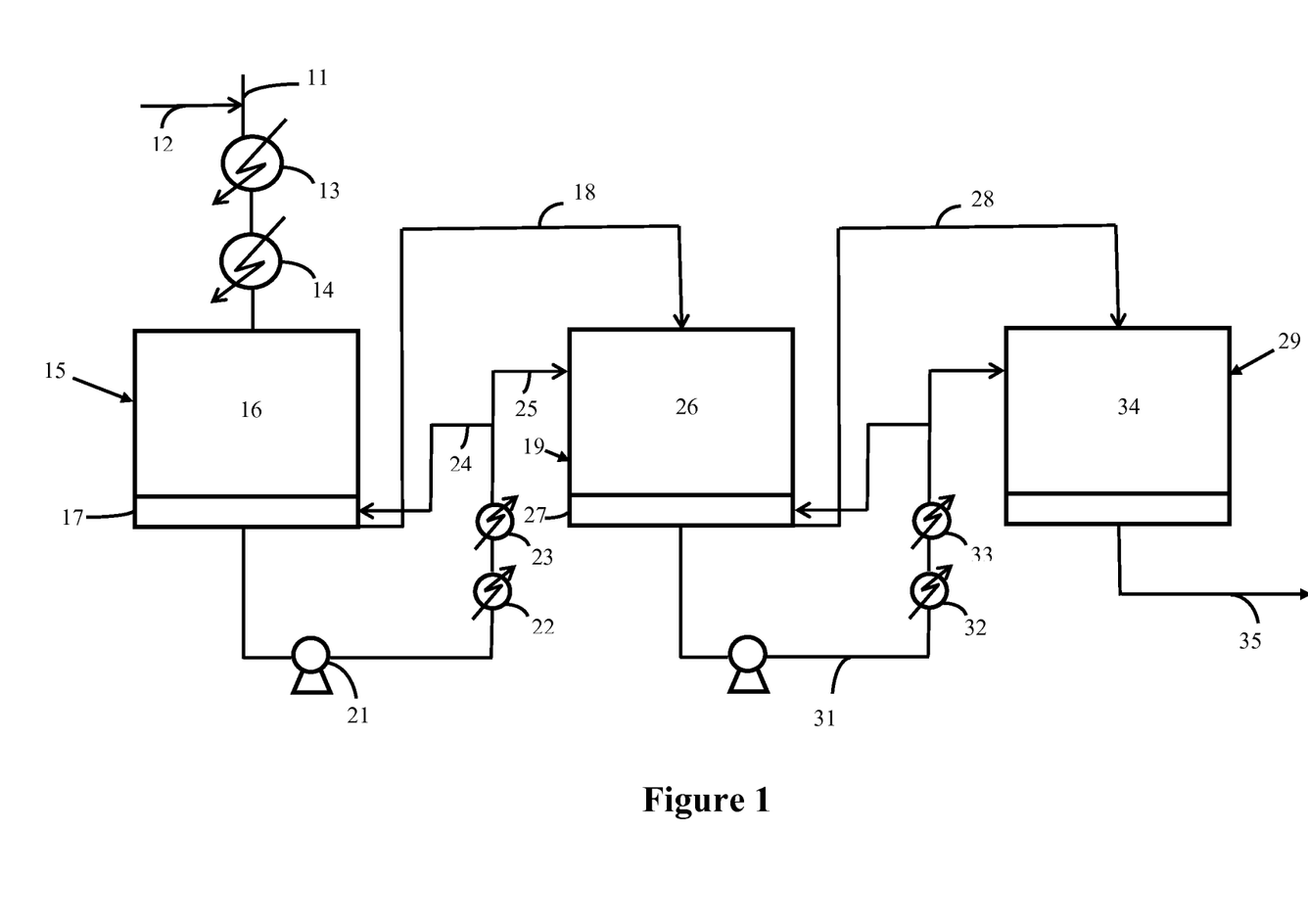
FIG. 1 is a flow diagram of a multi-stage process for producing cyclohexylbenzene according to a first embodiment of the invention.

Referring to the drawings, FIG. 1 illustrates a process for producing cyclohexylbenzene according to a first embodiment of the invention. In this process hydrogen from line 11 is mixed with benzene from line 12 and the resultant mixed stream is fed through first and second heat exchangers 13, 14 respectively before entering the top of a first, vertically disposed hydroalkylation reactor 15. In the first heat exchanger 13, the benzene/hydrogen mixture is heated by the reaction effluent from the final hydroalkylation reactor, whereas in the second heat exchanger 14, the benzene/hydrogen mixture is heated by low pressure steam. Collectively, the heat exchangers 13, 14 raise the temperature of the benzene/hydrogen mixture to about 100° C. to about 130° C.

In the reactor 15, the benzene/hydrogen mixture flows downwardly through a bed of a hydroalkylation catalyst which forms a first reaction zone 16 where the hydrogen reacts with the benzene to produce a mixed liquid/vapor phase first reaction effluent comprising cyclohexylbenzene and unreacted benzene and hydrogen, with at least part of the unreacted benzene being in the vapor phase. The hydroalkylation reaction is highly exothermic so that the temperature of the reaction effluent flowing out of the reaction zone 16 is typically from about 20° C. to about 70° C. higher than the temperature of the benzene/hydrogen mixture entering the reactor 15.

On leaving the first reaction zone 16, the first reaction effluent flows through a vapor/liquid contactor 17 located in the lower end of the reactor 15, where the effluent is cooled. A first portion of the reaction effluent is then fed by line 18 to the upper end of a second, vertically disposed hydroalkylation reactor 19, while the remainder of the effluent, after exiting the bottom of reactor, is pumped by a pump 21 through third and fourth heat exchangers 22, 23 respectively. In the third heat exchanger 22, the reaction effluent is cooled by heat exchange with the cold feed to a dehydrogenation reactor (not shown) for producing additional benzene from cyclohexane produced as a by-product of the hydroalkylation reaction. In the fourth heat exchanger 23, the reaction effluent is further cooled by heat exchange with cold water.

The third and fourth heat exchangers 22, 23 reduce the temperature of the effluent to about 100° C. to about 140° C. such that a liquid phase stream containing part of the cyclohexylbenzene in the effluent condenses to leave a residual mixed phase stream containing unreacted benzene and hydrogen and the remainder of the cyclohexylbenzene.

The liquid phase stream is recycled by line 24 to the vapor/liquid contactor 17 located in the lower end of the reactor 15 where the liquid phase stream contacts the mixed liquid/vapor phase reaction effluent leaving the reaction zone 16 and cools the reaction effluent by about 30° C. to about 130° C. before the reaction effluent exits the reactor 15.

The residual mixed phase stream is fed by line 25 to the upper end of the second hydroalkylation reactor 19 which houses a bed of a hydroalkylation catalyst forming a second reaction zone 26. In the second reaction zone 26, unreacted benzene and hydrogen in the residual mixed phase stream and the first effluent portion react to produce a second reaction effluent comprising additional cyclohexylbenzene and unreacted benzene and hydrogen. The second reaction effluent then flows out of the second reaction zone through a further vapor/liquid contactor 27 where the second reaction effluent is cooled. As in the case of the first reaction effluent, the cooled second effluent is divided into two portions; a first portion which is fed by line 28 to the upper end of a third, vertically disposed hydroalkylation reactor 29 and a second portion which is fed by line 31 to heat exchangers 32, 33.

The heat exchangers 32, 33 operate in the same manner as heat exchangers 22, 23 and cool the second effluent portion so as to condense a second liquid phase stream, which is recycled to the further vapor/liquid contactor 27, and leave a residual stream which is fed to the upper end of the third hydroalkylation reactor 29. The third hydroalkylation reactor 29 houses a bed of a hydroalkylation catalyst forming a third reaction zone 34 where unreacted benzene and hydrogen react to produce a third reaction effluent comprising still further cyclohexylbenzene. The third reaction effluent exits the bottom of the third reactor 29 through line 35 for further processing including removal of impurities, recovery of the cyclohexylbenzene and recovery and recycle of unreacted benzene and hydrogen.

Figure 2:
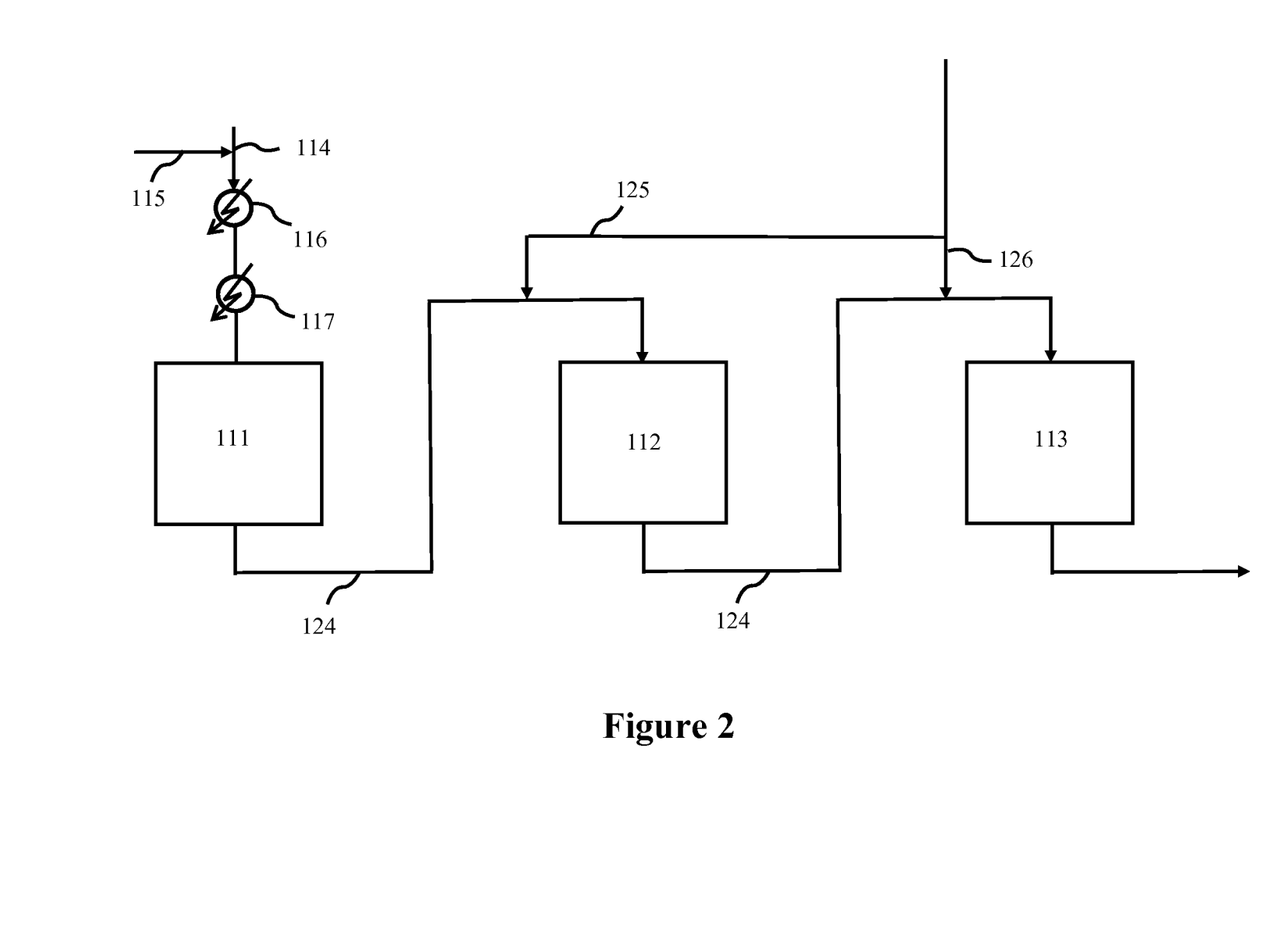
FIG. 2 is a flow diagram of a multi-stage process for producing cyclohexylbenzene according to a second embodiment of the invention.
Figure 3:
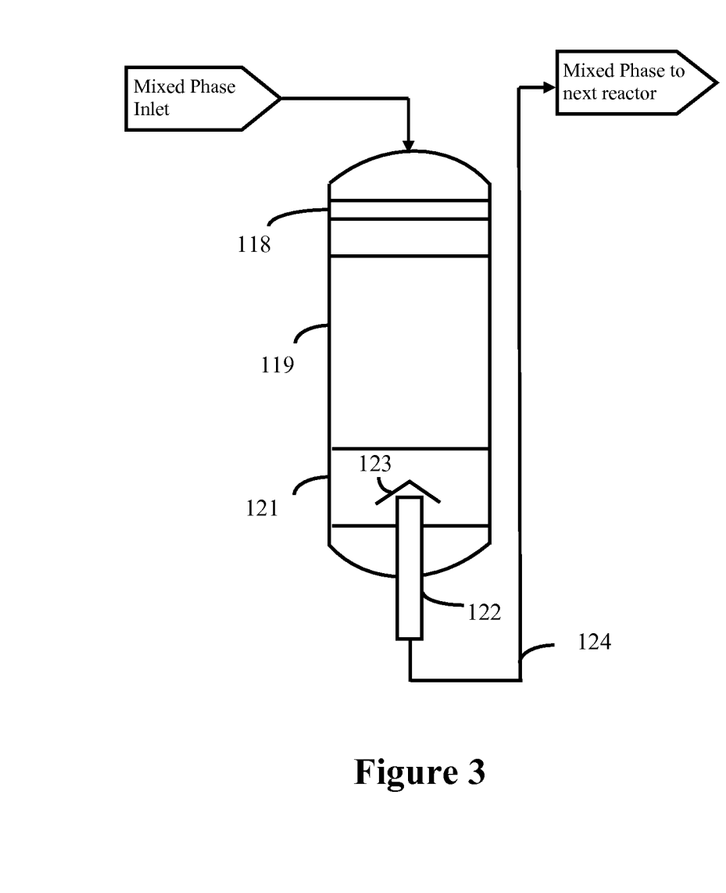
FIG. 3 is a schematic representation of one of the reactors employed in the process of the second embodiment.

FIGS. 2 and 3 illustrate a process for producing cyclohexylbenzene according to a second embodiment of the invention, in which the hydroalkylation is again conducted in three separate series-connected reactors 111, 112, 113 but with the hydrogen being fed separately to each reactor and being used to provide cooling of the reaction effluent flowing between the reactors. In particular, in the second embodiment, hydrogen from line 114 is mixed with benzene from line 115 and the resultant mixed stream is fed through first and second heat exchangers 116, 117 respectively before entering the top of the first, vertically disposed hydroalkylation reactor 111.

As shown in FIG. 3, one or more of the hydroalkylation reactors may include a set of trays 118 located in the top of the reactor above a catalyst-containing reaction zone 119 to assist in mixing of the reagents before they pass into the reaction zone. In the reaction zone 119, hydrogen and benzene in the reactor feed react to form a mixed liquid/vapor phase reaction effluent comprising cyclohexylbenzene and unreacted benzene and hydrogen, with at least part of the unreacted benzene being in the vapor phase. The reactor effluent then flows out of the reaction zone 119 into an outlet region 121 in the lower end of the reactor so that any liquid components condensing out of the reaction effluent settle in the base of the reactor. A perforated extraction tube 122 extends part of the way into the outlet region 121 such that its upper end is located beneath a conical cover 123 to prevent the reaction effluent flowing directly into the upper end of the tube 122. This covered tube arrangement facilitates stable mixed phase flow of the reaction effluent through the tube 122 via line 124 to the top of the next reactor in series.

In the case of the first and second reactors 111 and 112, the reaction effluent in each of lines 124 is mixed with additional hydrogen fed by lines 125 and 126 before the reaction effluent enters the reactors 112, 113. The additional hydrogen not only provides the hydrogen required for the hydroalkylation reaction but also lowers the pressure of the reaction effluent thereby causing vaporization of the benzene and rapid cooling of the effluent. Typically the hydrogen quenching reduces the temperature of the reaction effluent by at least 10° C., and preferably by at least 20° C.

Figure 4:
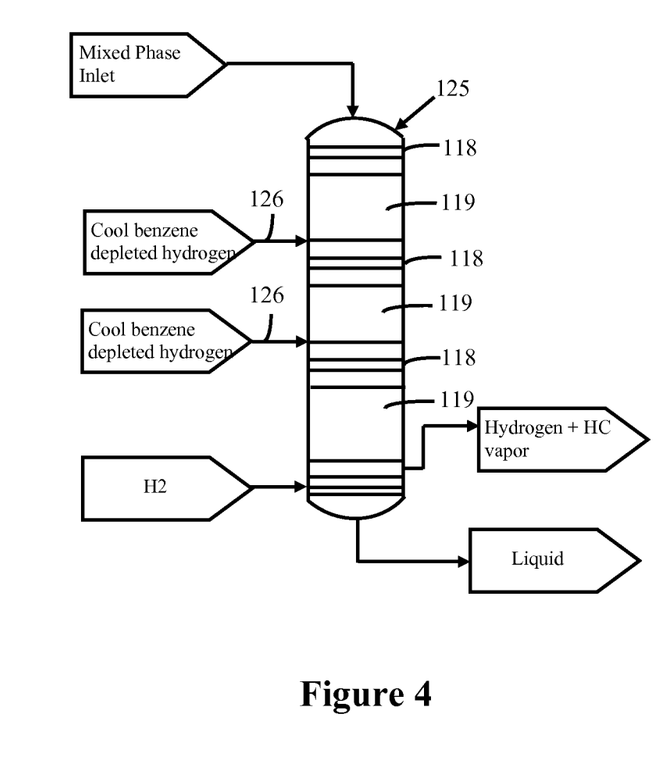
FIG. 4 is a schematic representation of a process according to a modification of the second embodiment.

In a modification of the second embodiment shown in FIG. 4, the reaction zones 119 are housed in a single reactor 125, with a set of trays 118 being mounted upstream of each reaction zone and hydrogen being introduced through lines 126 between the first and second and between the second and third reaction zones to effect interstage cooling of the reagents.

Figure 5:
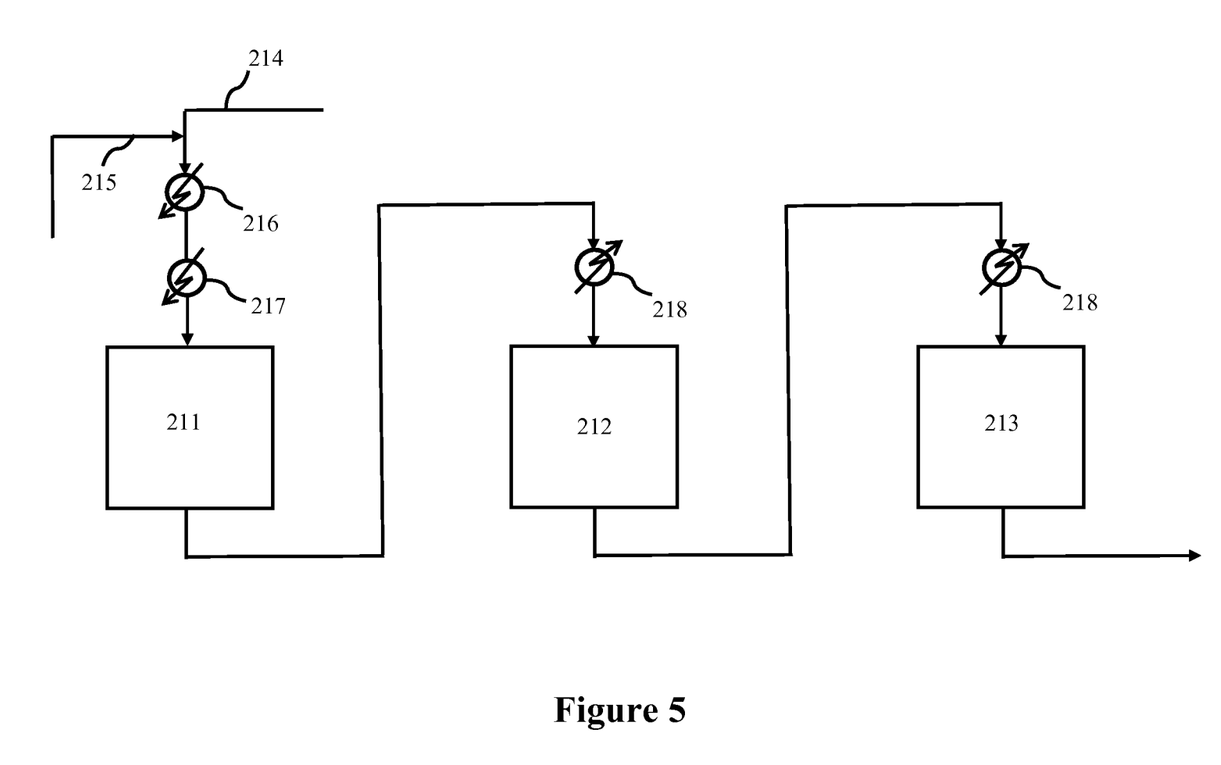
FIG. 5 is a flow diagram of a multi-stage process for producing cyclohexylbenzene according to a third embodiment of the invention.

A third embodiment of the invention is illustrated in FIG. 5, in which the hydroalkylation is again conducted in three separate series-connected reactors 211, 212, 213 but with all the hydrogen being fed to the first reactor as in the first embodiment. In particular, in the third embodiment, hydrogen from line 214 is mixed with benzene from line 215 and the resultant mixed stream is fed through first and second heat exchangers 216, 217 respectively before entering the top of the first, vertically disposed hydroalkylation reactor 111. Typically each reactor has the same construction and operation as the reactor shown in FIG. 3.

In the third embodiment, interstage cooling of the reaction effluent from the first and second reactors is effected by passing the mixed phase effluent from the first and second reactors 211, 212 through heat exchangers 218 located upstream of the second and third reactors 212, 213 and operated to cool the effluent without condensing the unreacted benzene. The cooled mixed phase effluent is then passed directly into the upstream reactor.

The invention claimed is:

1. A process for producing cyclohexylbenzene comprising:
   (a) introducing hydrogen and benzene to a first hydroalkylation reaction zone containing a hydroalkylation catalyst;
   (b) operating said first hydroalkylation reaction zone under at least partly liquid phase conditions sufficient to effect hydroalkylation of at least a portion of the benzene in the presence of said hydroalkylation catalyst to produce a first mixture exiting the first reaction zone comprising a liquid phase and a vapor phase, wherein the first mixture comprises cyclohexylbenzene and unreacted benzene;
   (c) separating the first mixture into a first liquid effluent comprising cyclohexylbenzene and a portion of the unreacted benzene and a first vapor effluent comprising at least a portion of the unreacted benzene;
   (d) cooling at least a portion of the first vapor effluent to obtain a second liquid effluent containing at least a portion of the unreacted benzene; and (e) recycling at least a portion of the second liquid phase stream to the first hydroalkylation reaction zone or to contact the first mixture or to mix with the first liquid effluent.

2. The process of claim 1, wherein the benzene contained in the second liquid effluent is at least 1 wt % of the total weight of the first mixture.

3. The process of claim 1, wherein the benzene contained in the first liquid effluent is at least 3 wt % of the total weight of the first mixture.

4. The process of claim 1, wherein the benzene contained in the first liquid effluent is at least 10 wt % of the total weight of the first mixture.

5. The process of claim 1, further comprising:
(f) introducing at least a portion of the first liquid effluent and additional hydrogen to a second hydroalkylation reaction zone containing a hydroalkylation catalyst and connected in series with the first hydroalkylation reaction zone; and
(g) operating said second hydroalkylation reaction zone under at least partly liquid phase conditions sufficient to effect hydroalkylation of at least a portion of the unreacted benzene in the first liquid effluent in the presence of said hydroalkylation catalyst to produce a third liquid effluent comprising cyclohexylbenzene.

6. The process of claim 1, wherein the cooling (d) is effected by passing the portion of the first vapor effluent through a heat exchanger, and the heat exchanger supplies heat to one of (i) a reboiler for a benzene distillation column and (ii) a dehydrogenation feed to a dehydrogenation reactor for converting cyclohexane produced as a byproduct of the operating step (b) to benzene.

7. The process of claim 5, wherein each of said operating steps (b) and (g) is conducted at a temperature of about 100° C. to about 250° C. and a pressure of about 100 kPa to about 7,000 kPa.

8. The process of claim 1, wherein the hydroalkylation catalyst comprises at least one molecular sieve and at least one hydrogenation metal.

9. A process for producing cyclohexylbenzene comprising:
(a) introducing hydrogen and benzene to a first hydroalkylation reaction zone containing a hydroalkylation catalyst;
(b) operating said first hydroalkylation reaction zone under at least partly liquid phase conditions sufficient to effect hydroalkylation of benzene in the presence of said hydroalkylation catalyst to produce a mixed liquid/vapor phase first effluent comprising cyclohexylbenzene and unreacted hydrogen and benzene, wherein at least a portion of the unreacted benzene is in the vapor phase;
(c) removing said mixed phase first effluent from said first hydroalkylation reaction zone;
(d) cooling at least a portion of the mixed phase first effluent removed from said first hydroalkylation reaction zone by heat exchange so as to supply heat to one of (i) a reboiler for a benzene distillation column and (ii) a dehydrogenation feed to a dehydrogenation reactor for converting cyclohexane produced as a byproduct of the operating steps (b) and (f) to benzene;
(e) introducing at least a portion of the cooled mixed phase first effluent to a second hydroalkylation reaction zone containing a hydroalkylation catalyst and connected in series with the first hydroalkylation reaction zone; and
(f) operating said second hydroalkylation reaction zone under at least partly liquid phase conditions sufficient to effect hydroalkylation of unreacted benzene in mixed phase first effluent in the presence of said hydroalkylation catalyst to produce a second effluent comprising cyclohexylbenzene.

10. The process of claim 9, wherein each of said operating steps (b) and (f) is conducted at a temperature of about 125° C. to about 250° C. and a pressure of about 100 kPa to about 7,000 kPa.

* * * * *